United States Patent [19]

Jahangiri-Famenini

[11] Patent Number: 5,694,948
[45] Date of Patent: Dec. 9, 1997

[54] DOUBLE LAYER ROLLING-UP OF CONDOMS

[76] Inventor: Hamid-Reza Jahangiri-Famenini, 58 Dolly Varden Blvd., Scarborough, Ontario, Canada, M1H 2K4

[21] Appl. No.: 739,788

[22] Filed: Oct. 30, 1996

[51] Int. Cl.[6] ............................................. A61F 6/02
[52] U.S. Cl. .................... 128/842; 128/844; 128/918
[58] Field of Search .......................... 128/842, 844, 128/918; 604/347–353

[56] References Cited

U.S. PATENT DOCUMENTS

| | | | |
|---|---|---|---|
| 2,586,674 | 2/1952 | Lonne | 128/844 |
| 5,070,890 | 12/1991 | Popurt | 128/844 |
| 5,284,159 | 2/1994 | Wilk | 128/844 |
| 5,314,447 | 5/1994 | Popurt | 128/844 |
| 5,425,379 | 6/1995 | Broad | 128/842 |

FOREIGN PATENT DOCUMENTS

| | | |
|---|---|---|
| 1321333 | 8/1993 | Canada. |
| 1321937 | 9/1993 | Canada. |

*Primary Examiner*—Michael A. Brown

[57] ABSTRACT

A condom and method of preparing condoms for packaging are disclosed. The rim of a conventional condom is moved close to the apex to create a double layered shaft. The shaft is then rolled from the posterior end to form a ring which lies behind the rim. A section of the shaft can be left unrolled to permit easier unrolling by the user. The method of condom preparation permits the condom to be applied in either direction.

2 Claims, 2 Drawing Sheets

DOUBLE LAYER ROLLING-UP OF CONDOMS

FIELD OF THE INVENTION

This invention relates to male condoms.

BACKGROUND TO THE INVENTION

The condom is a commonly used flexible and stretchable sheath worn on a penis during sexual intercourse to prevent and protect against, and reduce the chances of contracting sexually transmitted diseases and/or conception. The conventionally available condom is fundamentally a cylinder with a closed end, or apex, and an open end at which lies a rim. Condoms are available to consumers in a rolled-up state, to improve packaging, storage, handling, and use, among other reasons.

A conventional packaged condom is rolled up starting from the rim at the open end and proceeding in the direction of the closed end, the apex, until almost the entire shaft of the condom is consumed in the process. The final packaged product available to the consumer looks like a ring with a closed end.

A conventionally rolled-up condom is not, however, always easily and conveniently unrolled at the time of intended use by consumers, for various reasons. For example, the ring portion of a conventional condom, when rolled up, consists of many layers of the elastic condom material giving this portion more elastic resistance compared with the unrolled section of the condom shaft which consists of only one layer. The increased A conventionally rolled-up condom is not, however, always easily and conveniently unrolled at the time of intended use by consumers, for various reasons. For example, the ring portion of a conventional condom, when rolled up, consists of many layers of the elastic condom material giving this portion more elastic resistance compared with the unrolled section of the condom shaft which consists of only one layer. The increased elastic resistance of the ring portion exerts more pressure on the area of the penis on which the ring is resting, causing a depression; hence the ring "burrows in". During the unrolling process, the advancing ring is constantly confronted with the raised portion of the penis on the advancing side of the depression. This obstacle or "hump" must be overcome in order to unroll the condom. Since the ring lies in a depression, fingers unrolling the condom will quite often slip over the ring. At other times, a portion of unrolled shaft will become stretched over the ring and prevent further unrolling; when this occurs, pressure must be released to allow the ring to become free so that unrolling can begin again. In order to overcome the problem of burrowing in, the user must use more fingers, possible of both hands, to unroll the condom by placing the fingers inside and under the ring to lift it, which can cause the condom to rupture due to stretching or contact with sharp fingernails. If the unrolling process takes a relatively long time, it may cause anxiety, frustration, spoiling of the mood or loss of erection. This can serve as a deterrent to condom use.

SUMMARY OF THE INVENTION

The invention described within solves the problems encountered when unrolling conventional condoms.

In one aspect of the invention, the condom comprises a rim, a shaft, and an apex, which, in its rolled state prior to use, comprises a ring comprised of a rolled section of the shaft which lies behind the apex and the rim.

In another aspect, the invention comprises a condom rolled to permit it to be placed on the penis in either direction and easily unrolled.

In a further aspect, the invention comprises a method for preparing a condom for packaging comprising positioning a condom with a rim, shaft and apex in an extended state, moving the rim around the shaft towards the apex to a position behind the apex to create a double-layer along a substantial portion of the shaft, rolling the double layered portion of the shaft from the end farthest from the apex towards the apex to form a ring, and stopping the rolling action to leave the ring in a position behind the rim.

In a further aspect, the invention comprises a method for preparing for packaging a condom comprising a rim, a shaft, and an apex, comprising locating the rim adjacent the apex, rolling the portion of the shaft lying rearward of the rim around the shaft towards the apex to form a ring, and discontinuing the rolling when the ring approaches close to the rim.

Further aspects of the invention will become apparent from the following description.

DESCRIPTION OF THE DRAWINGS

FIG. 6.1A is a perspective, cutaway view of the condom with a double layered shaft;

FIG. 6.1B is a plan, cross-sectional view of the condom with a double layered shaft;

DESCRIPTION OF THE INVENTION

Figure 1:
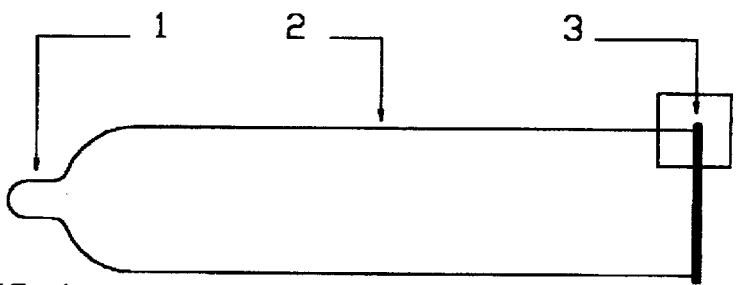
FIG. 1 is a plan, schematic view of a conventional condom.
Figure 2:
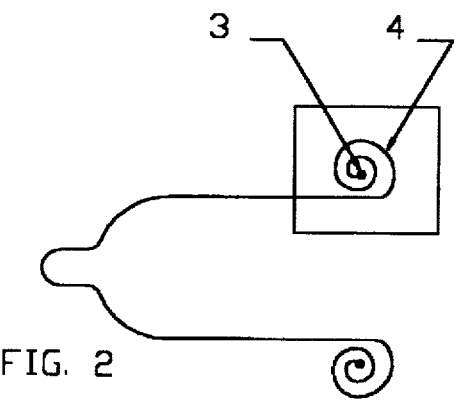
FIG. 2 is a plan, schematic view of the condom in a partially rolled state.

Referring to FIG. 1, the conventional condom consists of an apex 1, a shaft 2, and a rim 3. In conventional rolling, the rim 3 is rolled up the length of the shaft 2 to a point behind the apex, to form a ring 4 as shown in FIG. 2.

Figure 3:
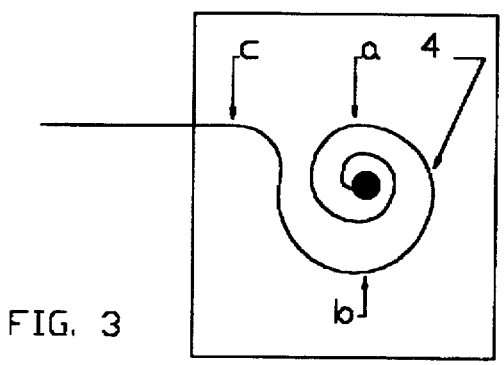
FIG. 3 is a plan, schematic view of the ring portion of the condom during unrolling.
Figure 4:
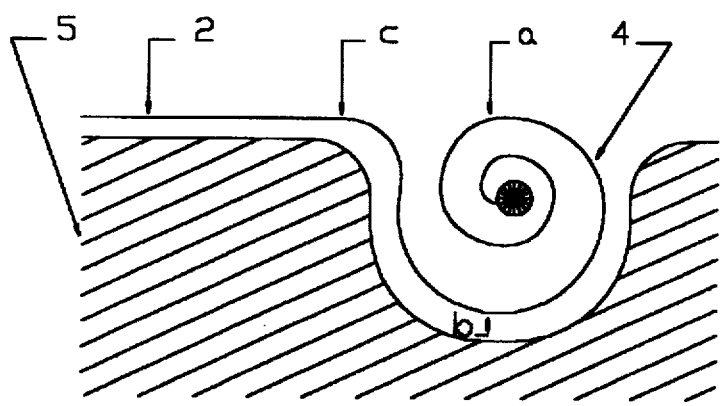
FIG. 4 is a plan, schematic cutaway view of a conventional condom on a penis during rolling.

In a conventional rolled-up condom, the ring portion consists of many layers of the elastic material over the rim giving this portion more elastic resistance compared with the unrolled section of the condom shaft which consists of only one layer. This is illustrated in FIGS. 1 and 2. When the condom is unrolled, the ring 4 exerts pressure on the penis 5 causing a depression. As illustrated in FIGS. 3 and 4, the level of the outermost layer of the ring at point 'a' is not substantially more elevated than the unrolled shaft at point 'c', due to "burrowing in". The result is that the fingers unrolling the condom will quite often slip over point 'a' as point 'a' is not substantially higher than point 'c' to allow a good grip.

At other times, point 'c' gets pulled over and stretched upon point 'a', which hinders or prevents further unrolling. Hence, the user must let go of the condom to permit it to relax, and then start unrolling it again.

Figure 5A:
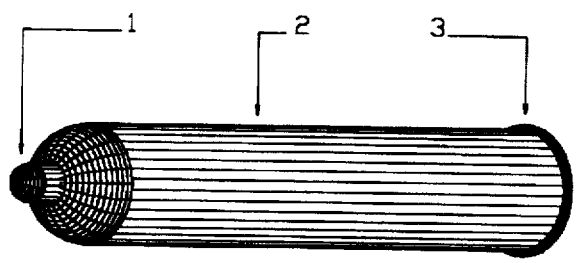
FIG. 5A is a perspective view of a condom prior to rolling.
Figure 5B:
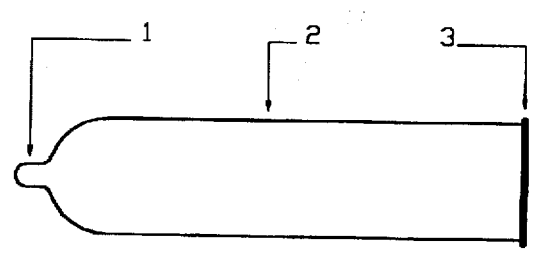
FIG. 5B is a plan, schematic view of a condom prior to rolling.

My invention is illustrated in FIGS. 5 to 7. As illustrated in FIG. 5A and 5B, a condom comprising an apex 1, shaft 2 and rim 3 is placed in an extended position in preparation for rolling.

Figure 6A:
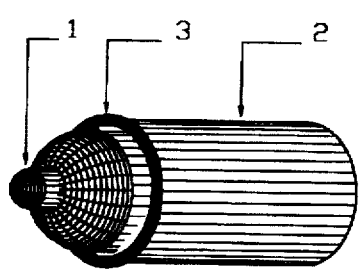
FIG. 6A is a perspective view of a condom with a double layered shaft according to the invention.
Figure 6B:
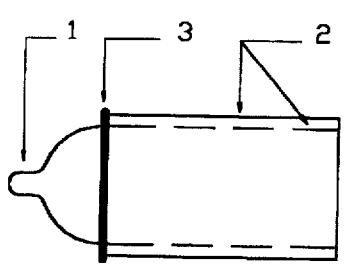
FIG. 6B is a plan, schematic view of a condom with a double layered shaft according to the invention.
Figure 7A:
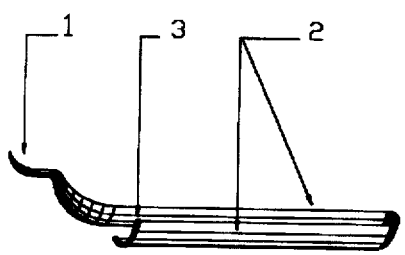
FIG. 7A is a perspective, schematic view of the condom with a ring formed from the shaft material.
Figure 7A:
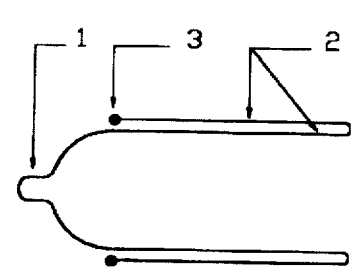
Figure 7A:
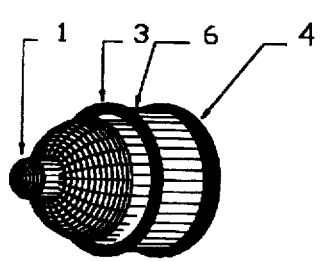
Figure 7B:
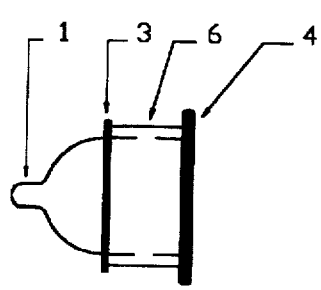
FIG. 7B is a schematic, cross-sectional view of a condom with a ring formed from the shaft material.

As illustrated in FIG. 6A, 6B, 6.1A and 6.1B, the rim is then drawn towards the apex to a point short of the apex to create a double layered shaft. As illustrated in FIG. 7A and 7B, beginning at the new end of the double layered shaft, distant from the apex, a ring 4 is formed by rolling the shaft around itself towards the apex to a point behind the rim 3. Preferably, a flap 6, comprising a portion of the shaft between the rim and the ring, is left free. When the user wishes to apply the condom, the fingers can grip the flap 6 which will both unroll the ring 4 and draw the rim 3 towards its ultimate position at the base of the penis.

A major advantage of this conformation of the condom is that it can be easily unrolled in either direction. If the user accidentally begins to apply the condom with the intended exterior of the apex on the interior of the condom, the condom will still easily unroll when the rim is gripped and the ring is allowed to unroll owing to the tension placed on the apex and the shaft.

It will be useful in certain applications to make the flap portion of the shaft thicker than the rest of the shaft to create strength and to make it easier to grasp.

This invention has many advantages over conventional condoms. It makes it easier and faster to apply a condom since less hand and finger manipulations are required. It reduces anxiety, nervousness and the potential loss of an erection. It may increase the use of condoms since there will be fewer deterrents owing to the improvements of the invention. Moreover, it may expand the choice of materials to be used in manufacturing condoms. When sheaths of some materials are rolled up, the layers stick together making them difficult to unroll from the conventional rolling up process. Using this method, even "sticky" materials will unroll fairly easily.

What is claimed is:

1. Method for preparing a condom for packaging, comprising:

(a) having a condom with a rim, shaft and apex, in an extended state;

(b) forcing the rim longitudinally along the shaft towards the apex to a position behind the apex to create a double-layer along a substantial portion of the shaft;

(c) rolling the double-layered portion of the shaft from the end farthest away from the apex towards the apex to form a ring;

(d) stopping the rolling action to leave the ring in a position behind the rim.

2. Method for preparing a condom comprising a rim, a shaft and an apex for packaging comprising locating the rim adjacent to the apex at the forward end of the condom to leave a double-layered portion of the shaft therebehind, rolling a portion of the shaft posterior to the rim beginning at the posterior end of the condom around the shaft towards the apex to form a ring, and discontinuing the rolling action when the ring is adjacent to the rim.

\* \* \* \* \*